United States Patent [19]  [11] Patent Number: 4,640,929
Mitsudera et al.  [45] Date of Patent: Feb. 3, 1987

[54] INSECTICIDALLY, ACARICIDALLY, AND NEMATOCIDALLY 2-AMINO-1,3-DITHIANE DERIVATIVES AND PESTICIDAL COMPOSITIONS THEREFOR

[75] Inventors: Hiroyuki Mitsudera; Kazuo Konishi, both of Osaka; Yasuo Sato, Kyoto, all of Japan

[73] Assignee: Takeda Chemical Industries, Ltd., Osaka, Japan

[21] Appl. No.: 525,635

[22] Filed: Aug. 23, 1983

[30] Foreign Application Priority Data

Aug. 27, 1982 [JP] Japan .................... 57-149633

[51] Int. Cl.$^4$ ............... A61K 31/38; C07D 339/00; C07D 409/00
[52] U.S. Cl. .................... 514/436; 514/79; 514/91; 514/97; 514/227; 514/237; 514/238; 514/326; 514/422; 544/145; 546/22; 546/284; 548/112; 548/119; 548/262; 548/527; 549/5; 549/21
[58] Field of Search ............ 424/200, 202, 248.4, 424/256, 274, 277; 544/145; 546/22, 284; 548/112, 119, 262, 527; 549/5, 21; 514/79, 91, 97, 227, 237, 238, 326, 422, 436

[56] References Cited
U.S. PATENT DOCUMENTS
3,318,936 5/1967 Sakai et al. .................. 549/21

OTHER PUBLICATIONS

Morrison et al., Textbook, "Organic Chemistry", Allyn and Bacon, Inc., Boston, 1973, p. 360.
Portnyagina et al, C.A., vol. 96, 1982, 96: 68506g, p. 568.
Portnyagina et al, C.A., vol. 96, 1982, 96: 35175v, p. 661.
Konishi, Kazuo, C.A., vol. 70, 1969, 70: 19997x, p. 1992.

Primary Examiner—Henry R. Jiles
Assistant Examiner—J. G. Mullins
Attorney, Agent, or Firm—Wegner & Bretschneider

[57] ABSTRACT

A novel 1,3-dithiane of the formula

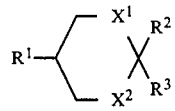

wherein $R^1$ is a di-substituted amino group; $R^2$ and $R^3$ are such that one of them is an electron-withdrawing group with the other being a hydrogen atom, a hydrocarbon group or heterocyclic group of the class consisting of thienyl, triazolyl, and pyridyl, which may optionally be substituted or that $R^2$ and $R^3$ taken together with the adjacent carbon atom form a spiro ring provided that at least one of $R^2$ and $R^3$ is a carbonyl group; $X^1$ and $X^2$ each is a sulfur atom and at least one of $X^1$ and $X^2$ may be oxidized, or a salt thereof, possesses very useful pesticidal actions.

12 Claims, No Drawings

INSECTICIDALLY, ACARICIDALLY, AND NEMATOCIDALLY 2-AMINO-1,3-DITHIANE DERIVATIVES AND PESTICIDAL COMPOSITIONS THEREFOR

The present invention relates to novel compounds having very useful pesticidal actions and, more particularly, to a 1,3-dithiane of the formula

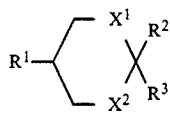  (I)

wherein $R^1$ is a di-substituted amino group; $R^2$ and $R^3$ are such that one of them is an electron-withdrawing group with the other being a hydrogen atom or a hydrocarbon group or heterocyclic group which may optionally be substituted or that $R^2$ and $R^3$ taken together with the adjacent carbon atom form a spiro ring provided that at least one of $R^2$ and $R^3$ is a carbonyl group; $X^1$ and $X^2$ each is a sulfur atom and at least one of $X^1$ and $X^2$ may be oxidized, or a salt thereof, methods for producing the same, and pesticidal compositions containing said compound or salt.

A variety of synthetic compounds having controlling effects on pests have heretofore been employed as pesticides but a large majority of the compounds are organophosphorus compounds, carbamates, or organochlorine compounds. It is well known that the use of such limited varieties of compounds causes various troubles such as an increased tolerance of pests to insecticides, and some of the abovementioned pesticides are not satisfactory in that while they have great pesticidal activity, they are also highly toxic to human beings, domestic animals and fish and sometimes even to natural enemies of pests so that they are liable to cause an unpredictable massive emergence of pests.

The intensive research undertaken by the present inventors to develop a new pest control agent which would be only sparingly toxic to human beings, domestic animals and fish, and even to natural enemies, safe to use, possessed of high activity for pest control, and completely different from the conventional insecticidal compounds in chemical structure resulted in the following discoveries. Thus, a novel 1,3-dithiane compound of the above general formula (I) or a salt thereof can be obtained by reacting a compound of the formula $$R^1CH(CH_2SSO_2R^4)_2 \quad (II)$$

wherein $R^1$ is as defined hereinbefore; and $R^4$ is a hydrocarbon group or a hydroxy group, or a salt thereof with a compound of the formula $$R^{2'}CH_2R^{3'} \quad (III)$$

wherein $R^{2'}$ and $R^{3'}$ are such that at least one of them is an electron-withdrawing group with the other being a hydrocarbon group or heterocyclic group which may optionally be substituted or that $R^{2'}$ and $R^{3'}$ taken together with the adjacent carbon atom form a ring provided that at least one of $R^2$ and $R^3$ is a carbonyl group, or a salt thereof; by reacting a compound of the formula

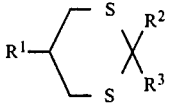  (IV)

wherein $R^1$, $R^2$ and $R^3$ are as defined hereinbefore, or a salt thereof with an oxidizing agent; by heating a compound of the formula

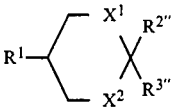  (V)

wherein $R^1$, $X^1$ and $X^2$ are as defined hereinbefore; and $R^{2''}$ and $R^{3''}$ are such that one of them is a group of the formula —COR or —COOR (where R is a hydrocarbon group which may optionally be substituted) with the other being an electron-withdrawing group, or a salt thereof in an organic solvent or by treating (V) with a base; by reacting a compound of the formula

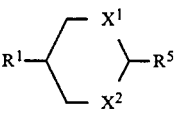  (VI)

wherein $R^1$, $X^1$ and $X^2$ are as defined hereinbefore; and $R^5$ is an electron-withdrawing group, or a salt thereof with a compound of the formula $$R^6W \quad (VII)$$

wherein $R^6$ is a hydrocarbon group or heterocyclic group which may optionally be substituted; and W is a halogen atom, in the presence of a base; or by alkylating a compound of the formula

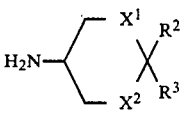  (VIII)

wherein $X^1$, $X^2$, $R^2$ and $R^3$ are as defined hereinbefore, or a salt thereof. It was also found that this novel 1,3-dithiane compound and salt meet the above-mentioned purposes and are more stable against acids and bases than are the pesticidal compounds hitherto available. The present invention is based on the above findings.

The present invention is therefore concerned with:
(1) a 1,3-dithiane (I) or a salt thereof;
(2) a method of producing a 1,3-dithiane of the formula

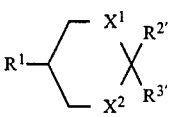  (IX)

wherein $R^1$, $X^1$, $X^2$, $R^{2'}$ and $R^{3'}$ are respectively as defined hereinbefore, or a salt thereof, characterized by reacting a compound (II) or a salt thereof with a compound (III) or a salt thereof;
(3) a method of producing a 1,3-dithiane of the formula

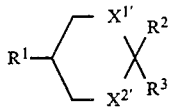

(X)

wherein $R^1$, $R^2$ and $R^3$ are respectively as defined hereinbefore; and $X^{1'}$ and $X^{2'}$ are sulfur atoms, at least one of which is oxidized, or a salt thereof characterized by reacting a compound (IV) or a salt thereof with an oxidizing agent;

(4) a method of producing a 1,3-dithiane (VI) or a salt thereof characterized by heating a compound (V) or a salt thereof in an organic solvent or treating the same (V) with a base;

(5) a method of producing a 1,3-dithiane of the formula

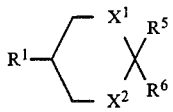

(XI)

wherein $R^1$, $X^1$, $X^2$, $R^5$ and $R^6$ are respectively as defined hereinbefore, or a salt thereof characterized by reacting a compound (VI) or a salt thereof with a compound (VII) in the presence of a base;

(6) a method of producing a 1,3-dithiane of the formula

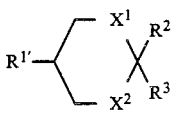

(XII)

wherein $R^2$ and $R^3$, $X^1$ and $X^2$ are respectively as defined hereinbefore; and $R^{1'}$ is a dialkylamino group, or a salt thereof, characterized by alkylating a compound (VIII); and (7) a pesticidal composition characterized by containing a 1,3-dithiane (I) or a salt thereof as an active ingredient.

Referring to the above formulas, $R^1$ is a di-substituted amino group and $R^{1'}$ is a dialkylamino group. The substituent groups on the amino group include, among others, lower alkyl groups of 1 to 4 carbon atoms, such as methyl, ethyl, propyl, isopropyl, etc., and cyano group, although methyl is preferred. The di-substituted amino group may form, by bondage of these substituents to each other, a cyclic amino group such as morpholino, pyrrolidino, etc. The electron-withdrawing (or electron attractive) group as represented by $R^2$, $R^{2'}$, $R^{2''}$, $R^3$, $R^{3'}$, $R^{3''}$ and $R^5$ means a group which "has a greater tendency to attract electrons than do hydrogen atoms in the molecule", thus being exemplified by nitrile, nitro, groups of the formula $COOR^7$ (where $R^7$ is a hydrogen atom or a hydrocarbon group) such as carboxyl and $C_{1-10}$ alkoxycarbonyl (e.g. methoxycarbonyl, ethoxycarbonyl, octyloxycarbonyl, etc.), $SO_2R$ (where R is as defined hereinbefore) such as $C_{6-10}$ arylsulfonyl (e.g. phenylsulfonyl, etc.), $CONR^8R^9$ [where $R^8$ and $R^9$ are the same or different and each is a hydrogen atom, $C_{1-4}$ alkylaminocarbonyl or a hydrocarbon group which may optionally be substituted or $R^8$ and $R^9$ combinedly represent a group of the formula $=CH-R^{1'}$ (where $R^{1'}$ is as defined hereinbefore) or taken together with the adjacent nitrogen atom represent a cyclic amino group] such as carbamoyl, mono- or di-$C_{1-15}$ alkylaminocarbonyl (e.g. methylaminocarbonyl, dimethylaminocarbonyl, ethylaminocarbonyl, diethylaminocarbonyl, n-propylaminocarbonyl, isopropylaminocarbonyl, diisopropylaminocarbonyl, n-butylaminocarbonyl, sec-butylaminocarbonyl, tert-butylaminocarbonyl, n-hexylaminocarbonyl, n-nonylaminocarbonyl, n-decylaminocarbonyl, n-tetradecylaminocarbonyl, etc.), amino-$C_{1-4}$ alkylaminocarbonyl (e.g. aminomethylaminocarbonyl, aminoethylaminocarbonyl, etc.), $C_{2-4}$ alkenylaminocarbonyl (e.g. vinylaminocarbonyl, allylaminocarbonyl, etc.), hydroxy-$C_{1-4}$ alkylaminocarbonyl (e.g. hydroxymethylaminocarbonyl, hydroxyethylaminocarbonyl, etc.), di-$C_{1-4}$ alkylaminomethyleneaminocarbonyl (e.g. dimethylaminomethyleneaminocarbonyl, etc.), $C_{3-6}$ cycloalkylaminocarbonyl (e.g. cyclopropylaminocarbonyl, cyclopentylaminocarbonyl, cyclohexylaminocarbonyl, etc.), 5- or 6-membered cyclic aminocarbonyl containing 1 to 3 nitrogen atoms which may be substituted with $C_{1-4}$ alkyl (e.g. piperazinocarbonyl, morpholinocarbonyl, pyprolidinocarbonyl, N-methylpiperazinocarbonyl, etc.), $C_{6-10}$ arylaminocarbonyl which may be substituted with $C_{1-4}$ alkyl or halogen (e.g. phenylaminocarbonyl, o-fluoro-p-chlorophenylaminocarbonyl, m-methylphenylaminocarbonyl, p-ethylphenylaminocarbonyl, etc.), $C_{1-4}$ alkylaminocarbonylaminocarbonyl (e.g. methylaminocarbonylaminocarbonyl, ethylaminocarbonylaminocarbonyl, etc.) and hydroxy-$C_{1-4}$ alkoxy-$C_{1-4}$ alkylaminocarbonyl (e.g. hydroxymethoxymethylaminocarbonyl, hydroxyethoxyethylaminocarbonyl, etc.), COR (where R is as defined hereinbefore such as $C_{1-4}$ alkylcarbonyl (e.g. methylcarbonyl, ethylcarbonyl, n-propylcarbonyl, etc.) and $C_{6-10}$ arylcarbonyl (e.g. phenylcarbonyl, etc.) or $PO(OR)_2$ (where R is as defined hereinbefore) such as di-$C_{1-4}$ alkoxyphosphoryl (e.g. dimethoxyphosphoryl, diethoxyphosphoryl, etc.) and di-$C_{6-10}$ aryloxyphosphoryl (e.g. diphenoxyphosphoryl, etc.), etc. $R^2$, $R^{2'}$, $R^3$, $R^{3'}$ and $R^6$ each represents a hydrocarbon group or heterocyclic group which may optionally be substituted, and the hydrocarbon group includes, among others, alkyl groups of 1 to 15 carbon atoms, such as methyl, ethyl, propyl, isopropyl, butyl, isobutyl, sec-butyl, tert-butyl, pentyl, hexyl, heptyl, octyl, nonyl, decyl, undecyl, dodecyl, tridecyl, tetradecyl, pentadecyl, etc.; cycloalkyl groups of 3 to 6 carbon atoms, such as cyclopropyl, cyclobutyl, cyclohexyl, etc.; alkenyl groups of 2 to 4 carbon atoms such as vinyl, allyl, 2-methallyl, 3-methallyl, 3-butenyl, etc.; cycloalkenyl groups of 3 to 6 carbon atoms, such as cyclopropenyl, cyclopentenyl, cyclohexenyl, etc.; aryl groups of 6 to 10 carbon atoms, such as phenyl, naphthyl, etc.; and aralkyl groups of 7 to 10 carbon atoms, such as benzyl, phenylethyl, etc., and the heterocyclic group include, among others, 5- to 6-membered heterocyclic groups containing oxygen, sulfur or/and nitrogen atoms as heteroatoms, such as thienyl, furyl, pyrazolyl, thiazolyl, isothiazolyl, oxazolyl, isooxazolyl, diazolyl, triazolyl, tetrazolyl, pyridyl, pyrimidyl, pyridazinyl, quinolyl, isoquinolyl, indolyl, etc. These hydrocarbon and heterocyclic groups may each contain one to several (preferable 1 to 2) substitutents such as nitro, amino, hydroxy, cyano, carbamoyl, carboxyl, sulfo, halogen (e.g. fluorine, chlorine, bromine, iodine, etc.), trifluoromethyl, methylenedioxy, lower alkoxy groups of 1 to 4 carbon atoms (e.g. methoxy, ethoxy, propoxy, isopropoxy, butoxy, isobutoxy, sec-butoxy, tert-butoxy, etc.), hydroxy-$C_{1-4}$ alkoxy group (e.g. hydroxymethoxy, hydroxyethoxy, etc.), phenoxy, benzoyl, halogenobenzoylaminocarbonylamino, halogenophenylaminocarbonylamino, etc. Moreover, the aryl, aralkyl, cycloalkyl and heterocyclic groups may have such substituents as the alkyls and aryls mentioned above. Representative examples of the hydrocarbon group and heterocyclic group which may optionally be substituted, are $C_{6-10}$ aryl which may be substituted with halogen, nitro, amino, methylenedioxy, $C_{1-4}$ alkoxy, $C_{1-4}$ alkyl, trifluoromethyl, phenoxy, halogenobenzoylaminocarbonylamino and/or halogenophenylaminocarbonylamino (e.g. phenyl, naphthyl, o-, m- or p-chloro, bromo or fluorophenyl, 2, 3-, 2, 4-, 2,5-, 2, 6- or 3, 4-dichloro or bromophenyl, o-, m- or p-nitrophenyl, o-, m- or p-methoxyphenyl, 3-nitro-4-methoxy- or 3-methoxy-4-nitrophenyl, o-, m- or p-trifluorophenyl, o-, m- or p-phenoxyphenyl, 2, 3- or 3, 4- methylenedioxyphenyl, o-, m- or p-aminophenyl, o-, m- or p-methyl or ethyl-phenyl, 2, 3-, 2, 4-, 2, 5- or 3, 4-dimethylphenyl, o-, m- or p-chlorophenylaminocarbonylaminophenyl, 2,6-difluoro or bromobenzoylaminocarbonylaminophenyl, etc.), $C_{1-6}$ alkyl (e.g. methyl, ethyl, propyl, isopropyl, butyl, i-butyl, sec-butyl, tert-butyl, pentyl, hexyl etc.), 5- or 6-membered heterocyclic group containing 1 to 3 hetero atoms selected from nitrogen and sulfur (e.g. pyrrolyl, diazolyl, triazolyl, pyridyl, pyrimidyl, thienyl, thiazolyl, thiadiazolyl, etc.) and the like. Referring to $R^2$ and $R^3$, and $R^{2'}$ and $R^{3'}$, each pair taken together with the adjacent carbon atom, may form a ring provided that at least one member of each pair is a carbonyl group, and examples of such ring include 5- to 6-membered alicyclic rings containing 1 to 2 oxo groups such as cyclohexanone, cyclohexanedione, cyclopentanone, cyclopentanedione, etc. and 5- to 6-membered heterocyclic rings containing 1 to 3 oxo groups such as pyrazolone, pyridazinetrione, pyridone, oxazolone, pyrrolidone, piperidone, etc. And these rings may optionally be substituted by the above-mentioned alkyl groups, halogens, amino, hydroxy, groups of the formula —N=CH—$R^{1'}$ (where $R^{1'}$ is as defined hereinbefore), etc. One of $R^2$ and $R^3$ may be a hydrogen atom. $R^4$ means a hydrocarbon group or a hydroxy group, and the hydrocarbon group is exemplified by the groups mentioned for $R^2$ and $R^3$. $R^{2''}$ and $R^{3''}$ are such that one of them is a group of the formula —COR or COOR. The hydrocarbon groups which may optionally be substituted, as represented by R, are such groups as those mentioned for $R^2$ and $R^3$. The hydrocarbon groups and the hydrocarbon groups which may optionally be substituted, as represented by $R^7$, $R^8$ and $R^9$, are such groups as those mentioned for $R^2$ and $R^3$. The cyclic amino group formed by $R^8$ and $R^9$ taken together with the adjacent nitrogen atom includes 5- to 6-membered cyclic amino groups such as piperazino, morpholino, pyrrolidino, etc. and these cyclic amino groups may be substituted for example by lower alkyl groups such as those mentioned hereinbefore. $X^1$ and $X^2$ each is a sulfur atom which may optionally be oxidized and $X^{1'}$ and $X^{2'}$ are such that at least one of them is an oxidized sulfur atom.

The objective compound (I) of the present invention exists as isomers when the carbon atom in 2-position of its 1,3-dithiane nucleus is an asymmetric carbon atom but all of these isomers as well as the mixture thereof fall within the scope of the present invention. Moreover, when an acidic group (e.g. COOH) exists in the substituent of $R^2$, $R^3$, the objective compound (I) may form a salt, for example, with an alkali metal or alkaline earth metal such as sodium, potassium, calcium, magnesium, etc. Further, at the basic group in the substituent of $R^2$, $R^3$ and/or the di-substituted amino group $R^1$, the compound (I) may form a salt with a mineral acid such as hydrochloric acid, phosphoric acid, sulfuric acid, etc. or an organic acid such as oxalic acid, acetic acid, benzoic acid, etc. Furthermore, at the di-substituted amino group $R^1$, the objective compound (I) may form a quaternary ammonium salt with an alkyl halide (of 1 to 4 carbon atoms) such as methyl iodide, methyl bromide, ethyl bromide, methyl chloride, ethyl chloride, etc.

Representative species of the objective compound (I) include 1,3-dithianes of the formula

(Ia)

[wherein $R^{1'}$ is as defined hereinbefore; and $R^{2a}$ and $R^{3a}$ are such that one of them is a cyano group with the other being a chlorine-substituted phenyl group or a group of the formula —$CONHR^{8a}$ (wherein $R^{8a}$ is a lower alkyl group of 1 to 4 carbon atoms)] and salts thereof, 1, 3-dithianes of the formula

(Ib)

wherein $R^{1'}$ is as defined above and $R^{2b}$ is a di-$C_{1-4}$-alkylaminocarbonyl group and salts thereof, and 1, 3-dithianes of the formula

(Ic)

wherein $R^{1'}$ is as defined above and $R^a$ is phenyl group or a $C_{1-4}$ alkyl group and salts thereof.

The compound (I) according to the present invention is effective in controlling sanitary pests and insects and mites parasitizing animals or plants and displays strong pesticidal activity as a contact poison when applied directly to the animals or plants parasitized by such pests. A more outstanding characteristic of this compound (I) is that it displays strong pesticidal effects when such pests expose themselves to it by sucking, gnawing or otherwise contacting the plants which were caused to absorb the compound (I) from their roots, leaves, stems, etc. Such properties are advantageous in the control of sucking or grawing insects and mites.

Moreover, the compound (I) of the present invention is sparingly toxic to plants and fish, thus possessing properties valuable and safe for use as an agricultural pest control agent. The compound (I) and compositions containing (I) are particularly effective in the control of harmful insects of the order Hemiptera such as *Eurydema rugosa, Scotinophara lurida, Riptortus clavatus, Stephanitis nashi, Laodelphax stiatellus, Nephotettix cincticeps, Unaspis yanonensis, Aphis glycines, Lipaphis pseudobrassicae, Brevicoryne brassicae* and *Aphis gossypii* insects of the order Glossata such as *Spodoptera litura*,

*Plutella xylostella, Pieris rapae crucivora, Chilo suppressalis, Plusia nigrisigna, Halicoverpa assulta, Leucania separata, Mamestra brassicae, Adoxophyes orana, Syllepte derogata, Cnaphalocrocis medinalis* and *Phthorimaea operculella,* insects of the order Coleoptera such as *Epilachna vigintioctopunctata, Aulacophora femoralis, Phyllotreta striolata, Oulema orgzae* and *Echinocnemus squameus,* insects of the order Diptera such as *Musca domestica, Culex pipiens pallens, Tabanus trigonus, Hylemya antiqua* and *Hylemya platura,* insects of the order Orthoptera such as *Locusta migratoria* and *Gryllotalpa africana,* harmful insects of the order *Blattella germanica* and *Periplaneta fuliginosa,* mites such as *Tetranychus urticae, Panonychus citri, Tetranychus kanzawai, Tetranychus cinnabarinus, Pansnychus ulmi* and *Aculus pelekassi,* nematodes such as *Aphelenchoides besseyi,* and so on.

In using the compound (I) according to the present invention as an insecticidal/acaricidal agent, it can be used in any application form in which an agricultural chemical can be made available. Thus, depending on the intended use, one or more species of compound (I) are either dissolved or dispersed in a suitable liquid vehicle or admixed with or adsorbed on a suitable solid vehicle and the resulting composition is made available in any of such forms as emulsifiable concentrate, oil, wettable powder, dusts, granules, tablets, aerosol mist, ointment, etc. There may also be added to these preparations such additives as emulsifiers, suspending agents, extenders, penetrants, wetting agents, thickners, stabilizers, etc. as necessary. These preparations can be produced by the known methods.

The proportion of the active agent (I) in such an insecticidal/acaricidal preparation depends on the intended use and application. In the case of an emulsifiable concentrate or wettable powder, the range of about 10 to 90 weight percent is desirable, while the range of about 0.1 to 10 weight % is suitable for an oil or dust. Granules may preferably contain about 1 to 20 weight % of (I). However, deviations from such concentration ranges are permissible for practical uses. In using the emulsifiable concentrate or wettable powder, it is preferable to dilute the concentrate or powder to a suitable concentration (e.g. 100- to 100000-fold), for example with water.

The liquid vehicle that may be employed includes, among others, water and organic solvents such as alcohols (e.g. methyl alcohol, ethyl alcohol, ethylene glycol, etc.), ketones (e.g. acetone, methyl ethyl ketone, etc.), ethers (e.g. dioxane, tetrahydrofuran, cellosolve, etc.), aliphatic hydrocarbons (e.g. gasoline, kerosin, kerosene, fuel oil, machine oil, etc.), aromatic hydrocarbons (e.g. benzene, toluene, xylene, solvent naphtha, methylnaphthalene, etc.), halogenated hydrocarbons (e.g. chloroform, carbon tetrachloride, etc.), acid amides (e.g. dimethylformamide, etc.), esters (e.g. ethyl acetate, butyl acetate, glycerin fatty acid esters, etc.), nitriles (e.g. acetonitrile, etc.), etc. and these vehicles can be used singly or in combination. The solid vehicle includes, among others, vegetable powders (e.g. soybean flour, tobacco powder, wheat flour, saw dust, etc.), mineral powders (e.g. clays such as kaolin, bentonite, terra alba, clay, agalmatolite, etc., talc, silicates such as diatomaceous earth, mica powder, etc.), alumina powder, sulfur powder, active carbon, etc. These solid vehicles may be used singly or in combination. The ointment bases that can be used includes polyethylene glycols, pectin, fatty acid esters of polyols such as glycerin monostearate, etc., cellulose derivatives such as methylcellulose, sodium alginate, bentonite, higher alcohols, polyols such as glycerin, vaseline, white vaseline, liquid paraffin, lard, vegetable oils, lanolin, dehydrated lanolin, hydrogenated oils, resins. These bases may be used singly or in combination, with or without addition of surfactants, etc.

The surfactants which may be employed as emulsifiers, extenders, penetrants, dispersants, etc. include, among others, polyoxyalkyl aryl ethers (e.g. Nonal ®, Takemoto Yushi K.K. Japan), alkylsulfates (e.g. Emal 10 ®, Emal 40 ® Atlas Co., Ltd., Japan), alkysulfonates (e.g. Neogen ®, Neogen T ®, Daiichi Kogyo Seiyaku K.K., Japan; Neopellex ®, Kao Atlas Co., Ltd., Japan), polyethylene glycol ethers (e.g. Nonipol 85 ®, Nonipol 100, Nonipol 160, Sanyo Kasei K.K., Japan), polyol esters (e.g. Tween, Tween 80, Kao Atlas Co., Ltd., Japan), etc. The compound according to the present invention may be used in combination or admixture with other kinds of insecticides (e.g. pyrethrin, organophosphorus, carbamate and natural insecticides), acaricides, nematocides, herbicides, plant growth hormones, plant growth regulators, fungicides (e.g. copper, organochlorine, organosulfur, phenolic and other fungicides), synergists, attractants, repellents, pigments, fertilizers, etc.

The objective compound (I) of the present invention can be produced, for example by the following processes.

PROCESS A

In the first place, a compound (II) or a salt thereof is reacted with a compound (III) or a salt thereof to give a 1,3-dithiane (IX) or a salt thereof.

The starting material compounds (II) and (III) may each be a free compound or may be used in the form of a salt such as those mentioned for compound (I). Each molar equivalent of compound (II) is reacted with one or slightly more than one equivalent of compound (III). Generally, this reaction is preferably conducted in a suitable solvent, such as water, alcohols (e.g., methanol, ethanol, n-propanol, isopropyl alcohol, n-butanol, etc.), aromatic hydrocarbons (e.g. benzene, toluene, xylene, etc.), halogenated hydrocarbons (e.g. methylene chloride, chloroform, carbon tetrachloride, etc.), ethers (e.g. ethyl ether, dioxane, tetrahydrofuran, etc.), ketones such as acetone, methyl ethyl ketone, etc., nitriles (e.g. acetonitrile, etc.), acid amides (e.g. dimethylformamide, etc.), esters (e.g. ethylacetate), sulfoxides (e.g. dimethyl sulfoxide), and other organic solvents. If necessary, a mixture of water with an aromatic hydrocarbon or halogenated hydrocarbon can be employed. The reaction may be accelerated by adding a base to the solvent. Examples of the base include tertiary amines (e.g. triethylamine, pyridine, γ-collidine, 4-dimethylaminopyridine, DBU (1,8-diazabicyclo[5,4,0]undeca-7-ene), etc.), hydroxides, carbonates and bicarbonates of alkali metals or alkaline earth metals and alkoxides of alkali metals (e.g. sodium carbonate, potassium carbonate, sodium hydrogen carbonate, sodium hydroxide, potassium carbonate, sodium alkoxide, etc.), and organic metal salts (e.g. n-butyllithium). The reaction may be conducted more advantageously, in some cases, in the presence of the base and a phase transfer catalyst (a quaternary ammonium salt such as triethylbenzylammonium chloride, tri-n-octylmethylammonium chloride, trimethyldecylammonium chloride, etc.).

While this reaction proceeds at room temperature (0°-40° C.), it may be accelerated by heating the reaction system at a suitable temperature (60° to 100° C.). The reaction generally goes to completion in a few minutes to several hours. After completion of the reaction, the desired compound (I) can be isolated and purified by the per se conventional procedure, for example by washing the reaction mixture directly with water or removing the solvent, extracting the residue with an organic solvent such as toluene, and washing the extract with water, followed by dehydration over a desiccant such as anhydrous sodium sulfate and removal of the solvent.

PROCESS B

A compound (IV) or a salt thereof is reacted with an oxidizing agent to produce a 1,3-dithiane (X) or a salt thereof.

The salt of compound (IV) may be one of the kinds mentioned for compound (I). The oxidizing agent is optional only if the desired reaction can be accomplished. Thus, for example, hydrogen peroxide, potassium permanganate, sodium metaperiodate, ceriumammonium nitrate, and organic peracids such as m-chloroperbenzoic acid, etc. Each molecular equivalent of said compound (IV) or salt thereof is reacted with 1.0 to 5.0 equivalents, preferably 1.1 to 4.2 equivalents, of the oxidizing agent. The reaction is preferably conducted in a solvent, such as halogenated hydrocarbons (e.g. methylene chloride, chloroform, carbon tetrachloride, etc.), alcohols (e.g.methanol, ethanol, etc.), ketones (e.g. acetone, etc.), nitriles (e.g. acetonitrile, etc.), organic acids (e.g. acetic acid, etc.), water, etc. While the reaction proceeds under cooling or at room temperature ($-30°$ C. to $+40°$ C.), the reaction may be accelerated by heating the reaction mixture at a suitable temperature (60° to 100° C.). The reaction goes to completion generally in 30 minutes to 12 hours and, preferably, 1 to 3 hours. After completion of the reaction, the product compound (X) can be isolated and purified by the per se known procedure, for example by washing the reaction mixture directly with water or by removing the solvent, extracting the residue with an organic solvent such as chloroform, and washing the extract with water, followed by dehydration over a desiccant such as anhydrous sodium sulfate and removal of the solvent.

PROCESS (C)

The compound (V) or a salt thereof is either heated in an organic solvent or reacted with a base to produce a 1,3-dithiane (VI) or a salt thereof.

The compound (V) may be a free compound or may be used in the form of a salt such as those mentioned for compound (I).

The compound (V) or salt thereof is heated in an organic solvent such as those mentioned for Process (A) at a temperature of generally 40° to 100° C. and preferably 40° to 60° C. The heating is continued generally for 1 to 10 hours and preferably for 2 to 4 hours. As an alternative method, each molar equivalent of the compound (V) or salt thereof is reacted with 0.5 to 8.0 molar equivalents, preferably 1.0 to 1.5 equivalents, of a base. The base may for example be one of those mentioned for Process (A). This reaction with the base is conducted for 0.5 to 6 hours or preferably for 1 to 2 hours. The base may be permitted to act on (V) or salt thereof in a solvent such as, for example, water, alcohols (e.g. methanol, ethanol, n-propanol, isopropyl alcohol, n-butanol, etc.), armatic hydrocarbons (e.g. benzene, toluene, xylene, etc.), halogenated hydrocarbons (e.g. methylene chloride, chloroform, etc.), ethers (dioxane, tetrahydrofuran, etc.), ketones (e.g. acetone, etc.), nitriles (e.g. acetonitrile, etc.), acid amides (e.g. dimethylformamide, etc.), sulfoxides (e.g. dimethyl sulfoxide, etc.), etc. Preferred solvents are ethanol, n-propanol, dioxane, acetonitrile, dimethylformamide, dimethyl sulfoxide, etc. Generally, the base is preferably permitted to act at room temperature (0° to 40° C.). The product compound (I) can be isolated and purified by the per se known procedures such as solvent extraction, concentration, pH adjustment, distillation, crystallization, recrystallization, chromatography, etc.

PROCESS (D)

A compound (VI) or a salt thereof is reacted with a compound (VII) in the presence of a base to give a 1,3-dithiane (XI) or a salt thereof.

The compound (VI) can be used in the free form or in the form of a salt such as those mentioned for compound (I). The base may be selected from among those mentioned for Process (A), although such other reagents as Grignard reagents (e.g. methylmagnesium iodide, ethylmagnesium chloride, phenylmagnesium bromide, etc.) and alkyllithium compounds (e.g. n-butyllithium) can also be employed. Each molar equivalent of said compound (VI) or salt thereof is reacted with 1 to 3 molar equivalents, preferably 1 to 2 equivalents, of said compound (VII). This reaction may be conducted in a solvent such as hydrocarbons (e.g. n-hexane), ethers (e.g. ethyl ether, dioxane, tetrahydrofuran, etc.), aromatic hydrocarbons (e.g. benzene, toluene, etc.), acid amides (e.g. dimethylformamide, etc.), sulfoxides (e.g. dimethyl sulfoxide, etc.). Preferred solvents are n-hexane, tetrahydrofuran, dimethyl sulfoxide, etc. This reaction is conducted generally at $-70°$ to $+30°$ C. and preferably at $-30°$ to $+20°$ C. The reaction time is 1.0 to 10 hours and preferably 2.0 to 4.0 hours. The product compound (XI) or salt thereof is isolated and purified by the per se known procedure.

PROCESS (E)

A compound (XIII) or a salt thereof is alkylated to a 1,3-dithiane (XII) or a salt thereof. The salt of compound (XIII) may be a salt such as those mentioned for the product compound (I). Each molar equivalent of said compound (VIII) or salt thereof is reacted with 1 to 10 equivalents, preferably 1 to 5 equivalents of an alkylating agent. This reaction may be advantageously conducted in the presence of a base. The alkylating agent may be of any kind which does not cause side reactions, for example, alkyl halides (e.g. methyl iodide, ethyl iodide, propyl bromide, etc.), alkyl sulfates (e.g. dimethyl sulfate, etc.), Grignard reagents (e.g. methylammonium iodide, ethylmagnesium chloride, etc.), etc. Particularly preferred are methyl iodide, ethyl bromide, dimethyl sulfate, etc. Generally this reaction is preferably conducted in a solvent such as water, alcohols (e.g. methanol, ethanol, etc.), nitriles (e.g. acetonitrile, etc.), halogenated hydrocarbons (e.g. methyl iodide, ethyl bromide, chloroform, etc.), and aromatic hydrocarbons (e.g. benzene, toluene, xylene, etc.). Among them, preferred are ethanol, methyl iodide, ethyl bromide, benzene and toluene, for instance. The reaction temperature depends on the alkylating agent employed and the solvent used but generally the reaction is carried out at 40°–150° C., preferably at 80°–120° C. Generally, the reaction is complete in 0.5–48 hours, and a reaction period of 1.0–10 hours is particularly preferred. The compound (XII) thus produced can be isolated by the above-mentioned known methods.

PROCESS (F)

The desired compound (I) of this invention can also be produced by reacting a compound of the formula

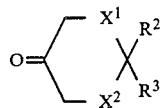

(XIII)

wherein the symbols are as defined above, or a salt thereof with a dialkylamine.

The compound (XIII) may be in the form of a salt with a mineral acid (e.g. hydrochloric acid, phosphoric acid, sulfuric acid, etc.) or an organic acid (e.g. oxalic acid, acetic acid, benzoic acid, etc.). This reaction is the so-called Wallach reaction and is preferably carried out in the manner of reduction in the presence, for instance, of formic acid or a formic acid derivative such as a formic acid salt (e.g. salt with an alkali metal, an alkaline earth metal, etc.), formamide or ammonium formate. Generally, this reaction is carried out at high temperatures (100°–200° C.) without using any solvent. The reaction can advantageously be promoted by the use of a catalyst such as magnesium chloride or ammonium sulfate, for instance. The reaction period can be selected in an adequate manner such that the desired compound can be obtained. The product produced can be isolated and purified by the known methods mentioned above.

The thus-obtained desired compound (I) of the present invention may further be purified, as desired, by such means as recrystallization or column chromatography. When the compound contains an amino group and it is difficult to crystallize the reaction product, the compound may preferably be isolated in the form of a salt form by adding an inorganic acid such as hydrogen chloride or an organic acid such as oxalic acid, p-toluenesulfonic acid or picric acid, for instance, and collecting the resulting crystalline salt. The salt produced here can be purified easily by recystallization from an alcohol or water.

The compounds (II), (III) and (VII) used as the starting materials in the above processes (A) to (E) can be synthesized by the known methods as described, for instance, in Japanese Patent Publication No. 18847/1970; J. Am. Chem. Soc., 63, 352 (1941); J. Org. Chem., 26, 2507 (1961); and Cyanides in Organic Reactions, A Literature Review, or modifications thereof. The compounds (IV), (V), (VI) and (VIII) are all novel compounds synthesized by the processes according to the present invention as mentioned above.

The following examples illustrate the invention but are by no means limitative of the invention.

EXAMPLE 1

To 20 ml of chloroform were added 1.6 g (0.01 mole) of diethyl malonate and 4.3 g (0.01 mole) of 1,3-bis(benzenesulfonylthio)-2-(N,N-dimethylamino)propane, and then 2.1 g (0.02 mole) of triethylamine was added thereto at room temperature. After completion of addition, the reaction was allowed to proceed at 40° C. for 4 hours. The reaction mixture was washed with two 20-ml portions of water, dried over anhydrous sodium sulfate and concentrated to dryness. The residue was heated in 20 ml of ether-hexane (1:1) for dissolution and the solution was allowed to stand in the cold overnight. The resulting crystalline precipitate was collected by filtration to give 2.7 g (90%) of 2,2-diethoxycarbonyl-5-(N,N-dimethylamino)-1,3-dithiane as light-yellow crystals melting at 38°–39° C.

EXAMPLE 2

To 20 ml of chloroform were added 1.52 g (0.01 mole) of p-chlorophenylacetonitrile and 4.3 g (0.01 mole) of 1,3-bis(benzenesulfonylthio)-2-(N,N-dimethylamino)propane, and then 3.1 g (0.02 mole) of 1,8-diazabicyclo[5,4,0]undeca-7-ene was added thereto at room temperature. After completion of addition, the reaction was allowed to proceed at 40° C. for 4 hours. The reaction mixture was washed with two 20-ml portions of water, dried over anhydrous magnesium sulfate and concentrated to dryness. The crystals thus obtained were heated in 10 ml of toluene for dissolution and the solution was allowed to stand in the cold overnight. The resulting crystalline precipitate was collected by filtration to give 2.6 g (87%) of 2-cyano-2-(p-chlorophenyl)-5-(N,N-dimethylamino)-1,3-dithiane as light-yellow crystals melting at 110°–111° C.

EXAMPLE 3

To 20 ml of chloroform were added 1.54 g (0.01 mole) of N-n-amylcyanoacetamide and 4.3 g (0.01 mole) of 1,3-bis(benzenesulfonylthio)-2-(N,N-dimethylamino)propane, and then 3.1 g (0.02 mole) of 1,8-diazabicyclo[5.4.0]undeca-7-ene was added thereto at room temperature. After completion of addition, the reaction was allowed to proceed at 50° C. for 4 hours. The reaction mixture was washed with two 20-ml portions of water, dried over anhydrous magnesium sulfate and concentrated to dryness. The residue was dissolved in 20 ml of acetonitrile, and 0.9 g (0.01 mole) of oxalic acid was added to the solution. The mixture was stirred well. The resulting crystalline precipitate was collected by filtration and recrystallized from 95% ethanol to give 3.1 g (79.2%) of 2-cyano-2-(N-n-amyl)-carboxamido-5-(N,N-dimethylamino)-1,3-dithiane oxalate as light-yellow crystals melting at 195°–196° C.

EXAMPLE 4

To 20 ml of dimethyl sulfoxide were added 1.52 g (0.01 mole) of p-chlorophenylacetonitrile. Sodium hydroxide (0.5 g) was gradually added to the mixture with ice-cooling, followed by gradual addition of 3.6 g (0.01 mole) of sodium 2-dimethylamino-1,3-propanedithiosulfate with ice-cooling. After completion of addition, the reaction was allowed to proceed at 5° C. for 1 hour. The temperature was raised gradually and the reaction was allowed to proceed at 40° C. for 4 hours. To the reaction mixture are added 50 ml of chloroform and 50 ml of saturated aqueous sodium chloride. The organic and aqueous layers were separated. The organic layer was washed 5 times with saturated aqueous sodium chloride, dried over anhydrous magnesium sulfate and concentrated to dryness. To the residue was added 10 ml of toluene and the mixture was heated for dissolution. After decolorization, the solution was allowed to stand in the cold overnight. The resulting crystalline precipitate was collected by filtration to give 1.0 g (35%) of 2-cyano-2-(p-chlorophenyl)-5-(N,N-dimethylamino)-

1,3-dithiane as light-yellow crystals melting at 110°–111° C.

EXAMPLE 5

To 20 ml of ethanol were added 2.6 g (0.01 mole) of 2-cyano-2-ethoxycarbonyl-5-dimethylamino-1,3-dithiane, and then 0.73 g (0.01 mole) of diethylamine was added thereto. The reaction was allowed to proceed at 60° C. for 1 hour. After completion of the reaction, the solvent was removed under reduced pressure. To the residue were added 20 ml of acetonitrile and 0.9 g of anhydrous oxalic acid and the mixture was thoroughly stirred. The resulting crystalline precipitate was collected by filtration to give 1.7 g (61.4%) of 2-cyano-5-dimethylamino-1,3-dithiane oxalate as light-yellow crystals melting at 162°–164° C.

EXAMPLE 6

To 20 ml of dry tetrahydrofuran were added 1.3 g (0.01 mole) of 2-cyano-5-dimethylamino-1,3-dithiane and the mixture was cooled to −30° C. in a nitrogen gas stream. A solution of 16% n-butyllithium in hexane (4 ml) was added, and a solution of 1.3 g (0.01 mole) of n-propyl bromide in 10 ml of n-hexane was added dropwise over 15 minutes. After completion of addition, the temperature was gradually raised to room temperature over about 1 hour. The reaction was allowed to proceed at room temperature for 2 hours. To the reaction mixture were added 50 ml of water and 50 ml of ethyl acetate. The oil layer was separated, dried over anhydrous sodium sulfate and concentrated under reduced pressure. The residue was purified by column chromatography ($SiO_2$, chloroform). The product was isolated as an oxalic acid salt, yielding 1.86 g. (58.1%) of 2-cyano-2-n-propyl-5-dimethylamino-1,3-dithiane oxalate as white crystals melting at 170°–171° C.

EXAMPLE 7

In 120 ml of methanol were dissolved 3.0 g (0.01 mole) of 2-cyano-2-(4-chlorophenyl)-5-dimethylamino-1,3-dithiane. While the solution was maintained at 20° C., a solution of 2.2 g (0.0105 mole) of sodium metaperiodate in 35 ml of water was added dropwise over 30 minutes. The mixture was stirred at the same temperature for 30 minutes. After completion of the reaction, the insoluble matter was filtered off and the filtrate was concentrated under reduced pressure. The residue was stirred well with 50 ml of chloroform and 50 ml of water. The chloroform layer was then separated, dried over anhydrous sodium sulfate and concentrated under reduced pressure. The residue was stirred well with 20 ml of acetonitrile and 0.9 g of anhydrous oxalic acid. The resulting crystalline precipitate was collected by filtration to give 2.0 g (51.4%) of 2-cyano-2-(4-chlorophenyl)-5-dimethylamino-1,3-dithiane 1-oxide oxalate as white crystals melting at 142°–143° C.

Table 1 shows some representative species of compound (1) prepared by the procedures of Examples 1 through 7, together with their melting/boiling point and yield data. The Compounds No. 1 through 8 were those obtained in Examples 1 to 3. The compound numbers indicated in the following Examples and Experimental Examples correspond to the Compound Numbers given in Table 1. Of course, products of this invention are not limited to those specific compounds.

TABLE 1

$$\begin{array}{c} R^1 \diagdown \phantom{X} \diagup S \diagdown \phantom{X} \diagup R^2 \\ \phantom{XXX} C = C \\ \phantom{XXX} \diagup S \diagdown \phantom{XX} \diagdown R^3 \end{array}$$

| Compound No. | $R^1$ | $R^2$ | $R^3$ | Salt formed | melting point or boiling point (°C.) | Yield (%) | Example No. whose procedure is employed |
|---|---|---|---|---|---|---|---|
| 1 | Me₂N— | —CO₂Et | —CO₂Et | | 38–39 | 90 | 1–3 |
| 2 | Me₂N— | —CN | —CN | | 110~111 | 87 | 2 |
| 3 | Me₂N— | —CN | —CONHC₅H₁₁(n) | | 195–196 (decomp.) | 79.2 | 3 |
| 4 | Me₂N— | —CO₂Et | —CO₂Et | Oxalate | 121–123 | 90 | 1, 3 |
| 5 | Me₂N— | —CO₂Et | —CO₂Et | Hydrochloride | 138–139 | 90 | 1, 3 |
| 6 | Me₂N— | —CO₂Et | —H | | 135–140/0.3 mmHg | 41 | 5 |
| 7 | Me₂N— | —CO₂Et | —H | Oxalate | 144–145 | 41 | 5 |
| 8 | Me₂N— | —COMe | —H | | 123–127/0.3 mmHg | 36.5 | 5 |
| 9 | Me₂N— | —COMe | —H | Oxalate | 151–152 | 36.5 | 5 |
| 10 | Me₂N— | —COOH | —H | | 275–278 (decomp.) | 53.1 | 5 |
| 11 | Me₂N— | —COMe | —COOMe | Oxalate | 155–156 | 75.6 | 1, 3 |
| 12 | Me₂N— | —CO₂C₈H₁₇(n) | —CO₂C₈H₁₇(n) | Oxalate | 72–73 | 80.3 | 1, 3 |
| 13 | Me₂N— | —CO₂Et | —SO₂Ph | | 129–130 | 73.8 | 2 |
| 14 | Me₂N— | —CO₂Et | —CN | | 75–77 | 72.6 | 2 |
| 15 | Me₂N— | —CO₂Et | —CN | Oxalate | 148–150 | 72.6 | 2, 3 |
| 16 | Me₂N— | —CO₂C₈H₁₇(n) | —CN | Oxalate | 126–127 | 79.5 | 1, 3 |
| 17 | Me₂N— | —H | —CN | Oxalate | 162–164 | 36 | 5 |
| 18 | Me₂N— | —CN | —CN | | 122–124 (decomp.) | 58.1 | 1 |
| 19 | Me₂N— | —SO₂Ph | —CN | Oxalate | 153–155 | 41 | 2, 3 |
| 20 | Me₂N— | $\overset{O}{\underset{\parallel}{-}}P(OEt)_2$ | —CN | Oxalate | 125–126 | 65.0 | 2, 3 |
| 21 | Me₂N— | —C₃H₇(n) | —CN | Oxalate | 170–171 | 58.1 | 6 |
| 22 | Me₂N— | —C₆H₅ | —CN | Oxalate | 199–201 (decomp.) | 85.3 | 2, 3 |
| 23 | Me₂N— | 2-methylphenyl | —CN | Oxalate | 235–236 (decomp.) | 75.8 | 2, 3 |

TABLE 1-continued

| Compound No. | R¹ | R² | R³ | Salt formed | melting point or boiling point (°C.) | Yield (%) | Example No. whose procedure is employed |
|---|---|---|---|---|---|---|---|
| 24 | Me₂N— | 3-Me-C₆H₄ | —CN | Oxalate | 176–177 (decomp.) | 63.2 | 2, 3 |
| 25 | Me₂N— | 3-CF₃-C₆H₄ | —CN | Oxalate | 155–156 (decomp.) | 64.5 | 2, 3 |
| 26 | Me₂N— | 2,4-diMe-C₆H₃ | —CN | | 144–145 | 73.6 | 2 |
| 27 | Me₂N— | —CN | 2,5-diMe-C₆H₃ | Oxalate | 180–181 | 73.6 | 2, 3 |
| 28 | Me₂N— | —CN | 2-MeO-C₆H₄ | Oxalate | 219–220 (decomp.) | 51.2 | 2, 3 |
| 29 | Me₂N— | —CN | 3-PhO-C₆H₄ | Oxalate | 226–227 (decomp.) | 74.9 | 2, 3 |

TABLE 1-continued
| Compound No. | R¹ | R² | R³ | Salt formed | melting point or boiling point (°C.) | Yield (%) | Example No. whose procedure is employed |
|---|---|---|---|---|---|---|---|
| 30 | Me₂N— | —CN | 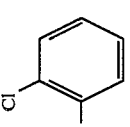 | Oxalate | 215-216 (decomp.) | 67.4 | 2, 3 |
| 31 | Me₂N— | —CN | 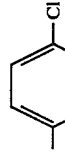 | Oxalate | 208-209 (decomp.) | 65.6 | 2, 3 |
| 32 | Me₂N— | —CN | 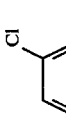 | Oxalate | 213-214 (decomp.) | 87 | 2, 3 |
| 33 | Me₂N— | —CN | 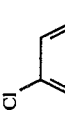 | Oxalate | 206-207 (decomp.) | 71.3 | 2, 3 |
| 34 | Me₂N— | —CN | 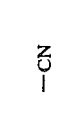 | Oxalate | 190-191 (decomp.) | 64.9 | 2, 3 |
| 35 | Me₂N— |  | —CN | Oxalate | 195-196 (decomp.) | 66.9 | 2, 3 |

TABLE 1-continued
| Compound No. | R¹ | R² | R³ | Salt formed | melting point or boiling point (°C.) | Yield (%) | Example No. whose procedure is employed |
|---|---|---|---|---|---|---|---|
| 36 | Me₂N— | 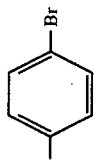 | —CN | Oxalate | 207–208 (decomp.) | 73.8 | 2, 3 |
| 37 | Me₂N— | 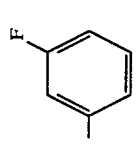 | —CN | Oxalate | 211–212 (decomp.) | 67.2 | 2, 3 |
| 38 | Me₂N— | 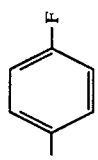 | —CN | | 205–206 (decomp.) | 82.3 | 2 |
| 39 | Me₂N— | 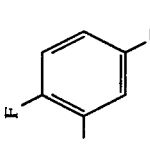 | —CN | Oxalate | 232–233 | 66.8 | 2, 3 |
| 40 | Me₂N— | 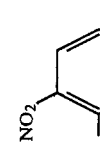 | —CN | | 131–132 | 74.0 | 2 |
| 41 | Me₂N— | —CN | 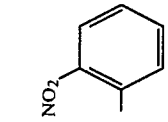 | Oxalate | 216–217 (decomp.) | 74.0 | 2, 3 |
| 42 | Me₂N— | —CN | 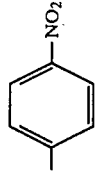 | Oxalate | 198–199 (decomp.) | 69.5 | 2, 3 |

TABLE 1-continued

| Compound No. | R¹ | R² | R³ | Salt formed | melting point or boiling point (°C.) | Yield (%) | Example No. whose procedure is employed |
|---|---|---|---|---|---|---|---|
| 43 | Me₂N— | —CN | -C₆H₄-NH₂ (p-aminophenyl) | Oxalate | 141-142 (decomp.) | 61.3 | 2, 3 |
| 44 | Me₂N— | —CN | naphthyl | Oxalate | 201-202 | 68.6 | 2, 3 |
| 45 | Me₂N— | —CN | pyridyl | Oxalate | 213-214 (decomp.) | 81.5 | 2, 3 |
| 46 | Me₂N— | thienyl | —CN | Oxalate | 210-211 (decomp.) | 74.4 | 2, 3 |
| 47 | Me₂N— | imidazolyl | —CN | Oxalate | 162-163 | 65.5 | 2, 3 |
| 48 | Me₂N— | —CONH₂ | —CN | | 168-169 (decomp.) | 76.3 | 2 |
| 49 | Me₂N— | —CN | —CONH₂ | Oxalate | 150-151 (decomp.) | 76.3 | 3 |
| 50 | Me₂N— | —CN | —CONHMe | | 90-91 | 68.5 | 2, 3 |
| 51 | Me₂N— | —CN | —CONHMe | Oxalate | 165-166 | 68.5 | 3 |
| 52 | Me₂N— | —CN | —CONHEt | | 101-102 | 71.3 | 2, 3 |
| 53 | Me₂N— | —CN | —CONHEt | Oxalate | 147-148 | 71.3 | 2, 3 |
| 54 | Me₂N— | —CN | —CONHPr(n) | | 74-75 | 67.4 | 2 |
| 55 | Me₂N— | —CN | —CONHPr(n) | Oxalate | 138-139 | 67.4 | 2, 3 |
| 56 | Me₂N— | —CN | —CONHPr(n) | Oxalate | 154-155 | 66.8 | 3 |
| 57 | Me₂N— | —CN | —CONHBu(n) | Oxalate | 143-144 | 64.9 | 3 |
| 58 | Me₂N— | —CN | —CONHBu(s) | Oxalate | 139-140 | 69.3 | 3 |
| 59 | Me₂N— | —CN | —CONHBu(t) | Oxalate | 164-165 | 65.6 | 3 |
| 60 | Me₂N— | —CN | —CONHC₆H₁₃(n) | Oxalate | 95-96 (decomp.) | 66.8 | 3 |

TABLE 1-continued

| Compound No. | R¹ | R² | R³ | Salt formed | melting point or boiling point (°C.) | Yield (%) | Example No. whose procedure is employed |
|---|---|---|---|---|---|---|---|
| 61 | Me₂N— | —CN | —CONHC₇H₁₅(n) | Oxalate | 89–90 | 70.9 | 3 |
| 62 | Me₂N— | —CN | —CONHC₈H₁₇(n) | Oxalate | 111–112 | 68.4 | 3 |
| 63 | Me₂N— | —CN | —CONHC₉H₁₉(n) | Oxalate | 91–92 | 71.2 | 3 |
| 64 | Me₂N— | —CN | —CONHC₁₀H₂₁(n) | | 47–48 | 64.3 | 2, 3 |
| 65 | Me₂N— | —CN | —CONHC₁₄H₂₉(n) | | 58–59 | 47.0 | 2, 3 |
| 66 | Me₂N— | —CN | —CONMe₂ | | 80–81 | 72.4 | 2, 3 |
| 67 | Me₂N— | —CN | —CONMe₂ | Oxalate | 177–178 (decomp.) | 72.4 | 3 |
| 68 | Me₂N— | —CN | —CONEt₂ | | 66–67 | 73.1 | 2, 3 |
| 69 | Me₂N— | —CN | —CONEt₂ | Oxalate | 184–185 (decomp.) | 73.1 | 3 |
| 70 | Me₂N— | —CN | —CONPr₂(i) | | 93–94 | 72.9 | 2, 3 |
| 71 | Me₂N— | —CN | —CONPr₂(i) | Oxalate | 187–188 (decomp.) | 72.9 | 3 |
| 72 | Me₂N— | —CN | —CONHCONHEt | | 137–138 | 61.3 | 2, 3 |
| 73 | Me₂N— | —CN | —CONHC₂H₄NH₂ | | 142–143 | 61.0 | 2, 3 |
| 74 | Me₂N— | —CN | —CONHCH₂CH=CH₂ | | 96–67 | 53.0 | 2, 3 |
| 75 | Me₂N— | —CN | —CONHC₂H₄OH | | 126–127 | 56.0 | 2, 3 |
| 76 | Me₂N— | —CN | —CONHC₂H₄OC₂H₄OH | | 121–122 | 72.9 | 2, 3 |
| 77 | Me₂N— | —CN | —CON=CHNMe₂ | | 143–144 |  | 2, 3 |
| 78 | Me₂N— | —CN |  —CONH—△ | | 137–138 | 48.0 | 2, 3 |
| 79 | Me₂N— | —CN | 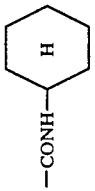 —CONH—⬡—H | | 132–133 | 67.0 | 2, 3 |
| 80 | Me₂N— | —CN | —CONHC₆H₅ | | 101–102 | 69.5 | 2, 3 |
| 81 | Me₂N— | —CN | 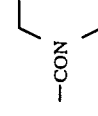 —CON⬠ | Oxalate | 197–198 | 70.4 | 3 |
| 82 | Me₂N— | —CN | 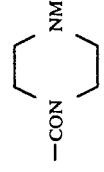 —CON⬡NMe | | 165–166 (decomp.) | 72.4 | 2, 3 |
| 83 | Me₂N— | —CONH₂ | —CONH₂ | | 190–191 (decomp.) | 64.2 | 2, 3 |
| 84 | Me₂N— | —CONHBu(n) | —CONHBu(n) | | 73–74 | 61.4 | 2, 3 |

TABLE 1-continued
| Compound No. | R¹ | R² | R³ | Salt formed | melting point or boiling point (°C.) | Yield (%) | Example No. whose procedure is employed |
|---|---|---|---|---|---|---|---|
| 85 | Me₂N— | 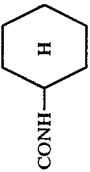 |  | | 183–184 | 62.4 | 2, 3 |
| 86 | Me₂N— | 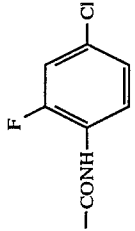 |  | | 146–147 | 63.6 | 2, 3 |
| 87 | Me₂N— | 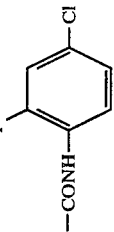 | | Oxalate | 169–171 | 59.6 | 3 |
| 88 | Me₂N— |  | | Oxalate | 168–170 | 39.8 | 3 |
| 89 | Me₂N— | 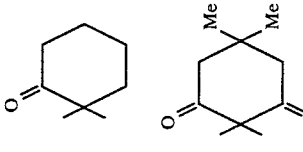 | | Oxalate | 180–181 (decomp.) | 78.2 | 3 |
| 90 | Me₂N— | 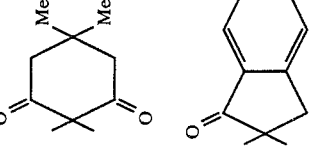 | | | 191–192 (decomp.) | 51.3 | 2, 3 |

TABLE 1-continued

| Compound No. | R¹ | R² | R³ | Salt formed | melting point or boiling point (°C.) | Yield (%) | Example No. whose procedure is employed |
|---|---|---|---|---|---|---|---|
| 91 | Me₂N— | | (structure: dimethyl barbiturate-like ring with N-H, N-H, C=O, C=O, gem-dimethyl) | Benzenesulfonate | 159–160 (decomp.) | 43.5 | 3 |
| 92 | Me₂N— | | (pyrazole with NH₂, N, NH, gem-dimethyl, C=O) | | 194–195 (decomp.) | 56.4 | 2, 3 |
| 93 | Me₂N— | | (Me₂NHC=N-substituted pyrazolone, gem-dimethyl) | | 190–191 | 98.0 | 2, 3 |
| 94 | (morpholine N—) | —CN | 4-bromophenyl | Oxalate | 172–173 (decomp.) | 72.4 | 2, 3 |
| 95 | (pyrrolidine N—) | —CN | 4-chlorophenyl | Oxalate | 195–196 | 69.7 | 2, 3 |
| 96 | Me—N(CN)— | —CO₂Et | —CO₂Et | | oil | 41.3 | 1 |
| 97 | Me₂⁺N(CN)— Br⁻ | —COMe | —CO₂Et | | 165–167 | 89.6 | 1, 2 |
| 98 | Me₃⁺N— I⁻ | —SO₂C₆H₅ | —CO₂Et | | 191–192 | 87.6 | 1, 2 |

TABLE 1-continued

| Compound No. | $R^1$ | $R^2$ | $R^3$ | Salt formed | melting point or boiling point (°C.) | Yield (%) | Example No. whose procedure is employed |
|---|---|---|---|---|---|---|---|
| 99 | Me$_3$N$^\oplus$—I$^\ominus$ | —CO$_2$Et | —CO$_2$Et | | 194–195 | 90.9 | 1, 2 |
| 100 | Et$_2$N— | —CN | 4-Cl-C$_6$H$_4$ | Oxalate | 194–195 | 87 | 3 |
| 101 | (n)Bu$_2$N— | —CN | 4-Cl-C$_6$H$_4$ | Oxalate | 179–180 | 79 | 3 |
| 102 | Me$_2$N— | —CN | 3,4-methylenedioxyphenyl | Oxalate | 222–223 | 75 | 3 |
| 103 | Me$_2$N— | —CN | 2-Br-C$_6$H$_4$ | Oxalate | 221–222 (decomp.) | 76 | 3 |
| 104 | Me$_2$N— | —CN | 2-Br-C$_6$H$_4$ | Oxalate | 112–113 | 76 | 2 |
| 105 | Me$_2$N— | —CN | 3-NO$_2$-C$_6$H$_4$ | Oxalate | 195–196 (decomp.) | 71 | 3 |

TABLE 1-continued

| Compound No. | R¹ | R² | R³ | Salt formed | melting point or boiling point (°C.) | Yield (%) | Example No. whose procedure is employed |
|---|---|---|---|---|---|---|---|
| 106 | Me$_2$N— | —CN | 2-NO$_2$-4-Me-phenyl with OMe | Oxalate | 223–224 (decomp.) | 69 | 3 |
| 107 | Me$_2$N— | —CN | 4-OMe-phenyl | Oxalate | 194–195 (decomp.) | 78 | 3 |
| 108 | Me$_2$N— | —CN | 3,5-dichlorophenyl | Oxalate | 225–226 (decomp.) | 69 | 3 |
| 109 | Me$_2$N— | —CN | 2-OMe-4-Me-6-NO$_2$-phenyl | | 145–146 | 64 | 2 |
| 110 | Me$_2$N— | —CN | 2-F-phenyl | Oxalate | 237–238 (decomp.) | 78 | 3 |
| 111 | Me$_2$N— | —CN | 2-F-phenyl | | 101–102 | 78 | 2 |

TABLE 1-continued

| Compound No. | R¹ | R² | R³ | Salt formed | melting point or boiling point (°C.) | Yield (%) | Example No. whose procedure is employed |
|---|---|---|---|---|---|---|---|
| 112 | Me₂N— | —CN | 3-fluorophenyl | | 68–69 | 69 | 2 |
| 113 | Me₂N— | —CN | 4-methylphenyl | Oxalate | 235–236 (decomp.) | 77 | 3 |
| 114 | Me₂N— | —CN | 4-methylphenyl | | 95–96 | 77 | 2 |
| 115 | Me₂N— | —CN | 3-chlorophenyl | | 94–95 | 81 | 2 |
| 116 | Me₂N— | —CN | 3-chlorophenyl | | 90–91 | 75 | 2 |
| 117 | Me₂N— | —CN | 2,6-difluoro-N′-(4-methylphenyl)biuret aryl | | 177–179 | 63 | 2 |
| 118 | Me₂N— | —CN | 4-chloro-N′-(4-methylphenyl)urea aryl | | 181–182 | 67 | 2 |

TABLE 1-continued

| Compound No. | R¹ | R² | R³ | Salt formed | melting point or boiling point (°C.) | Yield (%) | Example No. whose procedure is employed |
|---|---|---|---|---|---|---|---|
| 119 | Me₂N— | —CN | 4-Me-C₆H₄-NHCONHCO- (with 2,6-F₂) | Oxalate | 231–232 (decomp.) | 63 | 3 |
| 120 | Me₂N— | —COMe | —COMe | | 135–138/0.2 mm | 87 | 1 |
| 121 | Me₂N— | —COMe | —COMe | Oxalate | 178–179 | 87 | 3 |
| 122 | Me₂N— | —COMe | —CO-C₆H₅ | | 95–96 | 85 | 1 |
| 123 | Me₂N— | —COOEt | —CO-C₆H₅ | | 86–90 | 85 | 2 |
| 124 | Me₂N— | —CO-C₆H₅ | —CO-C₆H₅ | | 139–140 | 91 | 2 |
| 125 | Me₂N— | H | —CO-C₆H₅ | | 108–109 | 93 | 5 |
| 126 | Me₂N— | H | —CONH-(2-Me-C₆H₄) | | 163–164 | 86 | 5 |

TABLE 1-continued
R¹−CH(−CH₂−S−R²)(−CH₂−S(=O)−R³) structure
| Compound No. | R¹ | R² | R³ | Salt formed | melting point or boiling point (°C.) | Yield (%) | Example No. whose procedure is employed |
|---|---|---|---|---|---|---|---|
| 127 | Me₂N— | —CN | H | Oxalate | 150–151 (decomp.) | 66.1 | 7 |
| 128 | Me₂N— | —COMe | H | Oxalate | 138–140 (decomp.) | 65.6 | 7 |
| 129 | Me₂N— | —CO₂Et | —CO₂Et | Oxalate | 139–140 (decomp.) | 55.7 | 7 |
| 130 | Me₂N— | —CN | 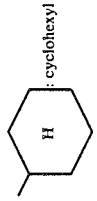 | Oxalate | 142–143 (decomp.) | 51.4 | 7 |
Me: methyl
Et: ethyl
Pr: propyl
Bu: butyl
ph: phenyl
H⟨cyclohexyl⟩ : cyclohexyl

EXAMPLE 8

Emulsifiable concentrate

An emulsifiable concentrate prepared by admixing the following components.

| Compound No. 2 | 20 wt. % |
|---|---|
| Xylene | 75 wt. % |
| Polyoxyethylene glycol ether (Nonipol ® 35) | 5 wt. % |

EXAMPLE 9

Wettable powder

A wettable powder prepared by admixing the following components.

| Compound No. 48 | 30 wt. % |
|---|---|
| Sodium ligninsulfonate | 5 wt. % |
| Polyoxyethylene glycol ether (Nonipol ® 35) | 5 wt. % |
| White carbon | 30 wt. % |
| Clay | 30 wt. % |

EXAMPLE 10

Dust

A dust prepared by admixing the following components.

| Compound No. 51 | 3 wt. % |
|---|---|
| White carbon | 3 wt. % |
| Clay | 94 wt. % |

EXAMPLE 11

Granules

A granular product prepared by admixing and granulating the following components.

| Compound No. 52 | 10 wt. % |
|---|---|
| Sodium ligninsulfonate | 5 wt. % |
| Clay | 35 wt. % |

EXPERIMENTAL EXAMPLE 1

Effect against Chilo suppressalis

Each test compound was made into an emulsifiable concentrate according to the formula of Example 8 and the concentrate was diluted with water to give an aqueous solution of 500 ppm concentration. Using a metered feed microsyringe, a 1 μl portion of this test solution was dripped onto the back of the abdomen of each 5-instar larva of Chilo suppressalis, whereby 50 μg/g of the test drug was administered. Then, the larvae were transferred to a Petri dish (9 cm across) and maintained in a room at 25° C. for 48 hours. Then, dead larva were counted. Using 10 larvae for each dose level, the experiment was carried out in duplicate. The results in terms of mortality rate are shown in Table 2.

$$\text{Mortality (\%)} = 100 - \frac{\text{Number of surviving larvae}}{\text{Number of test larvae}} \times 100$$

TABLE 2

| Compound No. | Chilo suppressalis 50 μg/g Mortality rate (%) | Compound No. | Chilo suppressalis 50 μg/g Mortality rate (%) | Compound No. | Chilo suppressalis 50 μg/g Mortality rate (%) |
|---|---|---|---|---|---|
| 1 | 100 | 47 | 100 | 84 | 100 |
| 2 | 100 | 48 | 100 | 85 | 100 |
| 3 | 100 | 49 | 100 | 86 | 100 |
| 4 | 100 | 50 | 100 | 88 | 100 |
| 5 | 100 | 51 | 100 | 90 | 100 |
| 6 | 100 | 52 | 100 | 91 | 100 |
| 8 | 100 | 53 | 100 | 92 | 100 |
| 9 | 100 | 54 | 100 | 93 | 100 |
| 12 | 100 | 55 | 100 | 100 | 100 |
| 13 | 100 | 56 | 100 | 102 | 90 |
| 14 | 100 | 57 | 100 | 103 | 100 |
| 15 | 100 | 58 | 100 | 104 | 100 |
| 16 | 100 | 59 | 100 | 105 | 100 |
| 17 | 100 | 60 | 100 | 106 | 100 |
| 18 | 100 | 61 | 100 | 108 | 100 |
| 19 | 100 | 62 | 100 | 109 | 100 |
| 20 | 100 | 63 | 100 | 110 | 100 |
| 21 | 100 | 64 | 100 | 113 | 100 |
| 22 | 100 | 65 | 100 | 114 | 100 |
| 23 | 100 | 66 | 100 | 115 | 100 |
| 26 | 100 | 67 | 100 | 116 | 100 |
| 27 | 100 | 68 | 100 | 119 | 100 |
| 28 | 100 | 69 | 100 | 120 | 100 |
| 29 | 100 | 70 | 100 | 121 | 100 |
| 30 | 100 | 71 | 100 | 122 | 100 |
| 31 | 100 | 72 | 100 | 123 | 100 |
| 32 | 100 | 73 | 100 | 124 | 100 |
| 33 | 100 | 74 | 100 | 125 | 100 |
| 34 | 100 | 75 | 100 | 127 | 100 |
| 35 | 100 | 76 | 100 | *1 | 0 |
| 37 | 100 | 77 | 100 | *2 | 0 |
| 39 | 100 | 78 | 100 | *3 | 0 |
| 40 | 100 | 79 | 100 | *4 | 0 |
| 41 | 100 | 80 | 100 | *5 | 0 |
| 44 | 100 | 81 | 100 | *6 | 10 |
| 45 | 100 | 82 | 100 | | |
| 46 | 100 | 83 | 100 | | |

Note:
*1–*6 are compounds employed as control, and have respectively the following chemical structures.

*1 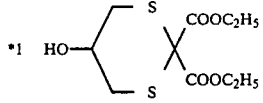

*2 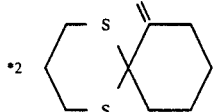

*3 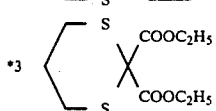

*4 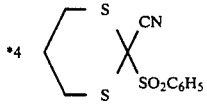

*5 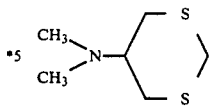

*6 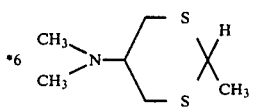

EXPERIMENTAL EXAMPLE 2

Effect against *Laodelphax striatellus*

Each test compound was made into an emulsifiable concentrate according to the formula of Example 8 and the concentrate was diluted with water to prepare a test liquid of 50 ppm concentration. This liquid was put in a 100 ml beaker and 8 paddy rice seedlings (7 days after germination) were dipped in the liquid for 10 seconds. Then, the seedlings were transferred to a test tube containing 1 ml of water and ten 3-instar larvae of *Laodelphax striatellus* were released into the tube. The test tube was maintained in a room (28° C.) for 24 hours, at the end of which time the larvae were investigated for survival. This experiment was carried out in duplicate and the results in terms of % mortality are shown in Table 3.

TABLE 3

| Compound No. | *Laodelphax striatellus* 50 ppm, Mortality rate (%) | Compound No. | *Laodelphax striatellus* 50 ppm, Mortality rate (%) |
|---|---|---|---|
| 20 | 65 | 114 | 65 |
| 34 | 95 | 116 | 85 |
| 60 | 65 | 119 | 45 |
| 61 | 80 | 122 | 90 |
| 62 | 85 | 123 | 75 |
| 63 | 100 | 124 | 100 |
| 64 | 58 | 125 | 85 |
| 66 | 75 | *1 | 0 |
| 74 | 75 | *2 | 0 |
| 86 | 90 | *3 | 0 |
| 90 | 60 | *4 | 0 |
| 104 | 95 | *5 | 0 |
| 105 | 70 | *6 | 0 |
| 113 | 85 | | |

(*1-*6 are of the same meaning as referred to in Table 2.)

EXPERIMENTAL EXAMPLE 3

Effect against *Spodoptera litura*

(a) Using a spray gun (spray pressure 1 kg/cm$^2$), soybean seedlings (10 days after germination) in a pot (9 cm in diameter) were sprayed with 20 ml of a 500 ppm aqueous dilution of the test compound (the emulsifiable concentrate of Example 8) (with 3,000 times of Dyne ®, an extender). Two hours after the treatment, 2 leaves were shorn off and each was placed in an ice cream cup (6 cm in diameter, 4 cm deep) and ten 3-instar larvae of *Spodoptera litura* were released into the cup. The cup was maintained in a room (25° C.) for 48 hours, at the end of which time the larvae were investigated for survivals. This experiment was carried out in duplicate and the results in terms of % mortality are shown in Table 4.

TABLE 4

| Compound No. | *Spodoptera litura*, 500 ppm Mortality rate (%) | Compound No. | *Spodoptera litura*, 500 ppm Mortality rate (%) |
|---|---|---|---|
| 1 | 100 | 65 | 70 |
| 16 | 60 | 66 | 70 |
| 34 | 100 | 67 | 80 |
| 35 | 60 | 68 | 80 |
| 48 | 100 | 70 | 60 |
| 49 | 100 | 73 | 60 |
| 50 | 80 | 74 | 60 |
| 51 | 90 | 75 | 80 |
| 52 | 90 | 83 | 100 |
| 53 | 80 | 107 | 50 |
| 54 | 60 | *1 | 0 |
| 55 | 60 | *2 | 0 |
| 57 | 80 | *3 | 0 |
| 59 | 80 | *4 | 0 |
| 60 | 70 | *5 | 0 |
| 61 | 80 | *6 | 0 |
| 63 | 90 | | |

(*1-*6 are of the same meaning as referred to in Table 2.)

EXPERIMENTAL EXAMPLE 4

Effect against *Unaspis yanonensis*

Each test compound was made into a wettable powder according to the formula of Example 9 and diluted with water (with 3,000 times of Dyne ®, an extender) to prepare an aqueous suspension of 500 ppm. This aqueous suspension was applied to 2-instar female larvae of *Unaspis yanonensis* (10 to 50 larvae) feeding on seedlings (2 months after germination) of trifoliate orange in a pot (9 cm in diameter) After the treatment, the pot was placed in a green house (25°–30° C.). On the 20th day after the treatment the number of surviving adults was investigated. This experiment was carried out in duplicate and the results in terms of % mortality are presented in Table 5.

In the above Experimental Examples 2 through 4, % mortality calculations were made by means of the formula given in Experimental Example 1.

TABLE 5

| Compound No. | *Unaspis yanonensis* 500 ppm, Mortality rate (%) |
|---|---|
| 42 | 65 |
| 66 | 62 |
| 117 | 71 |
| 119 | 52 |
| *1 | 0 |
| *2 | 0 |
| *3 | 0 |
| *4 | 0 |
| *5 | 0 |
| *6 | 0 |

(*1-*6 are of the same meaning as referred to in Table 2.)

EXPERIMENTAL EXAMPLE 5

Effect against *Tetranychus urticae*

Each test compound was made into an emulsifiable concentrate according to the formula of Example 8 and the concentrate was diluted with water (containing 3,000 times of Dyne ®, an extender) to prepare an aqueous solution of 500 ppm. Ten female larvae of *Tetranychus urticae* were used to infest kidney bean seedlings water-cultured in an ice cream cup. The cup was placed in a glass chamber (28° C.) for 24 hours and, then, 20 ml of the above aqueous solution was applied to the seedlings. After the treatment, the cup was returned to the glass chamber and the number of adults feeding on the foliage was investigated on the second day. This experiment was performed in duplicate and the % decrease of population was calculated by means of the equation given below. The results are shown in Table 6.

$$\% \text{ Decrease} = \frac{\text{Number of test mites} - \text{Number of survivals}}{\text{Number of test mites}} \times 100$$

TABLE 6

| Compound No. | Tetranychus urticae, 500 ppm Mortality rate (%) | Compound No. | Tetranychus urticae, 500 ppm Mortality rate (%) | Compound No. | Tetranychus urticae, 500 ppm Mortality rate (%) |
|---|---|---|---|---|---|
| 4 | 100 | 51 | 100 | 92 | 80 |
| 7 | 100 | 53 | 90 | 93 | 90 |
| 9 | 100 | 55 | 100 | 94 | 90 |
| 11 | 100 | 56 | 100 | 95 | 100 |
| 12 | 60 | 57 | 100 | 97 | 70 |
| 13 | 90 | 58 | 100 | 98 | 70 |
| 14 | 70 | 59 | 100 | 100 | 100 |
| 15 | 100 | 60 | 100 | 102 | 100 |
| 16 | 80 | 61 | 90 | 103 | 100 |
| 17 | 80 | 62 | 100 | 104 | 60 |
| 18 | 90 | 63 | 100 | 105 | 100 |
| 20 | 100 | 64 | 90 | 106 | 100 |
| 21 | 70 | 65 | 70 | 107 | 90 |
| 22 | 100 | 66 | 100 | 108 | 100 |
| 23 | 100 | 67 | 70 | 110 | 100 |
| 27 | 100 | 68 | 80 | 113 | 100 |
| 28 | 100 | 69 | 100 | 114 | 100 |
| 30 | 100 | 70 | 100 | 116 | 90 |
| 31 | 80 | 71 | 100 | 122 | 80 |
| 32 | 100 | 73 | 60 | 123 | 90 |
| 34 | 80 | 74 | 70 | 124 | 80 |
| 35 | 100 | 75 | 90 | 127 | 100 |
| 37 | 90 | 76 | 100 | 128 | 90 |
| 39 | 100 | 79 | 80 | 129 | 90 |
| 41 | 70 | 81 | 90 | *1 | 0 |
| 44 | 100 | 82 | 90 | *2 | 0 |
| 45 | 100 | 83 | 60 | *3 | 0 |
| 46 | 60 | 84 | 60 | *4 | 0 |
| 47 | 100 | 87 | 100 | *5 | 20 |
| 48 | 60 | 88 | 90 | *6 | 30 |
| 49 | 100 | 89 | 90 | | |
| 50 | 90 | 90 | 60 | | |

(*1-*6 are of the same meaning as referred to in Table 2.)

What we claim is:

1. A 1,3-dithiane compound of the formula

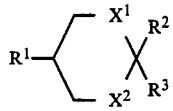

wherein

R$^1$ is a di-substituted amino group of the class consisting of di-C$_{1-4}$-alkylamino, morpholino, pyrrolidino and N(C$_{1-4}$-alkyl)CN; Groups R$^2$ and R$^3$ are such that one of these groups is an electron-withdrawing group of the class consisting of cyano, nitro, carboxyl, a C$_{1-10}$-alkoxycarbonyl, C$_{6-10}$-arylsulfonyl, carbamoyl, mono- or di-C$_{1-15}$-alkylaminocarbonyl, amino-C$_{1-4}$alkylaminocarbonyl, C$_{2-4}$ alkenylaminocarbonyl, hydroxy-C$_{1-4}$-alkylaminocarbonyl, di-C$_{1-4}$-alkylaminomethyleneaminocarbonyl, C$_{3-6}$-cycloalkylaminocarbonyl, piperazinocarbonyl, morpholinocarbonyl, pyrrolidinocarbonyl, N-methylpiperazinocarbonyl, C$_{6-10}$-arylaminocarbonyl which may be substituted with C$_{1-4}$-alkyl or halogen, C$_{1-4}$-alkylaminocarbonylaminocarbonyl, hydroxy-C$_{1-4}$-alkoxy-C$_{1-4}$-alkylaminocarbonyl, C$_{1-4}$-alkylcarbonyl, C$_{1-4}$-alkylcarbonyl, C$_{6-10}$-arylarbonyl, di-C$_{1-4}$-alkoxyphosphoryl and di-C$_{6-10}$-aryloxyphosphoryl group and the other group which R$_2$ and R$_3$ represent is a hydrogen atom, a hydrocarbon group of the class consisting of a C$_{1-15}$-alkyl, C$_{3-6}$-cycloalkyl, C$_{2-4}$-alkenyl, C$_{3-6}$-cycloalkenyl, C$_{6-10}$-aryl and phenyl-C$_{1-3}$-alkyl groups, or a heterocyclic group of the class consisting of thienyl, triazolyl, and pyridyl, said hydrocarbon or heterocyclic groups being optionally substituted by amino, hydroxy, cyano, carbamoyl, carboxyl, sulfo, halo, trifluoromethyl, methylenedioxy, C$_{1-4}$-alkoxy, hydroxy-C$_{1-4}$-alkoxy, phenoxy, benzoyl, halobenzoylaminocarbonylamino or halophenylaminocarboxylamino groups;

X$^1$ is —S— or —SO—;

X$^2$ is —S—; or a salt thereof.

2. A 1,3-dithiane compound of the formula

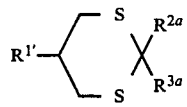

wherein R$^1$ is a di-C$_{1-4}$-alkylamino group and one of the groups R$^{2a}$ and R$^{3a}$ is cyano and the other is a chlorine-substituted phenyl group or group of the formula-CONHR$^{8a}$ in which R$^{8a}$ is a C$_{1-4}$-alkyl group, or a salt thereof.

3. A 1,3-dithiane compound, of the class consisting of 2,2-diethoxycarbonyl-5-(N,N-dimethylamino)-1,3-dithiane, 2-cyano-2-(N-n-amyl)carboxamido-5-(N,N-dimethylamino)-1,3-dithiane, 2-acetyl-2-methoxycarbonyl-5-(N,N-dimethylamino)-1,3-dithiane, 2,2-di(n-octyloxycarbonyl)-5-N,N-dimethylamino)-1,3-dithiane, 2-ethoxycarbonyl-2-benzenesulfonyl-5-(N,N-dimethylamino)-1,3-dithiane 2-cyano-2-ethoxycarbonyl-5-(N,N-dimethylamino)-1,3-dithiane, 2-cyano-2-(n-octyloxycarbonyl)-5-(N,N-dimethylamino)-1,3-dithiane, 2,2-dicyano-5-(N,N-dimethylamino)-1,3-dithiane, 2-cyano-2-benzenesulfonyI-5-(N,N-dimethylamino)-1,3-dithiane, 2-cyano-2-diethoxyphosphoryl-5-(N,N-dimethylamino)-1,3-dithiane, 2-cyano-2-carbamoyl1-5-(N,N-dimethylamino)-1,3-dithiane, 2-cyano-2-(N-n-heptyl) carboxamido-5-(N,N-dimethylamino);1,3-dithiane, cyano-2-(N-n-hexyl)carboxamido-5-(N,N-dimethylamino)-1,3-dithian2-cyano-2-(N-n-heptyl)carboxamido-5-(N,N-dimethylamino)-1,3-dithiane, 2-cyano-2-(N-n-octyl)carboxamido-5-(N,N-dimethylamino)-1,3-dithiane, 2-cyano-2-(N-n-nonyl)-carboxamido-5-(N,N-dimethylamino)-1,3-dithiane, 2-cyano-2-(N-n-decyl)carboxamido-5-(N,N-dimethylamino)-1,3-dithiane, 2-cyano-2-(N,N-tetradecyl)-carboxamido-5-(N,N-dimethylamino)-1,3 dithiane, 2-cyano-2-(N-ethylcarbamoyl)carboxamido-5-(N,N-dimethylamino)-1,3-dithiane, 2-cyano-2-[N-(2-aminoethyl)] carboxamido-5-(N,N-dimethylamino)-1,3-dithiane, 2-cyano-2-(N-allyl) carboxamido-5-(N,N-dimethylamino)1,3-dithiane, 2-cyano-2-[N-(2-hydroxyethyl)] carboxamido-5-(N,N-dimethylamino)1-3-dithiane, 2-cyano-2-[N-[2-(2-hydroxy)ethoxy]] carboxamido-5-(N,N-dimethylamino)-1,3-dithiane, 2-cyano-2-(N-dimethylaminomethylene)carboxamido-5-(N,N-dimethylamino)-1,3-dithiane, 2-cyano-2-(N-cyclopropyl)carboxamido-5-(N,N-dimethylamino)-1,3,-dithiane, 2-cyano-2-(N-cyclohexyl) carboxamido-5-(N,N-dimethylamino)-1,3-dithiane, 2-cyano-2-(N-phenyl)carboxamido-5-(N,N-dimethylamino)-1,3-dithiane, 2-cyano-2-pyrrolidinocarbonyl-5-(N,N-dimthylamino)-1,3-dithiane, 2-cyano-2-(4-methyl-piperazinocarbonyl)-5-(N,N-dimethylamino)-1,3 dithiane, 2,2-dicarbamoyl-5-(N,N-dimethylamino)-1,3-dithiane, 2,2-di[(N-n-butyl)carboxamido]5-(N,N-dimethylamino-1,3-dithiane,2,2-di[(N-cyclohexyl) carboxamido]-5-(N,N-dimethylamino)-1,3-dithiane,2,2-di[N-(4-chloro-3-fluoro)-phenyl]carboxamido]5-(N,N-imethylamino)-1,3-dithiane,2,2-diethoxycarbonyl-5-(N-cyano-N-methylamino)-1,3-dithiane, 2-acetyl-2-ethoxycarbonyl-5-(N-cyano-N-methylamino)-1,3-dithiane and 2,2-diethoxycarbonyl-5-(N,N-dimethylamino)-1,3-dithiane 1-oxide, or a salt thereof.

4. A compound as claimed in claim 1, wherein $R^1$ is a di-$C_{1-4}$ alkylamino group.

5. A compound as claimed in claim 1, wherein $X^1$ and $X^2$ are both sulfur atom.

6. A compound of the formula

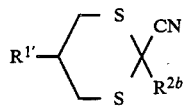

wherein $R^{1'}$ is a di-$C_{1-4}$ alkylamino group and $R^{2b}$ is a di-$C_{1-4}$ alkylaminocarbonyl group or a salt thereof.

7. A compound of the formula

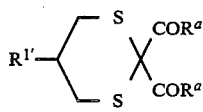

wherein $R^{1'}$ is a di-$C_{1-4}$ alkylamino group and $R^a$ is phenyl group or a $C_{1-4}$ alkyl group, or a salt thereof.

8. A compound as claimed in claim 6, which is 2-cyano-2-(N,N-diethylaminocarbonyl)-5-(N,N-dimethylamino)-1,3-dithiane.

9. A compound as claimed in claim 7, which is 2,2-dibenzoyl-5-(N,N-dimethylamino)-1,3-dithiane.

10. A pesticidal composition which contains in a carrier an insecticidally, acaridically or nematocidally effective amount of a 1,3-dithiane compound of the formula

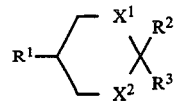

wherein
$R^1$ is a di-substituted amino group of the class consisting of d-$C_{1-4}$-alkylamino, morpholino, pyrrolidino and $N(C_{1-4}$-alkyl CN; $R^2$ and $R^3$ are such that one of them is an electron-withdrawing group of the class consisting of cyano, nitro, carboxyl, a $C_{1-10}$-alkoxycarbonyl, $C_{6-10}$-arylsulfonyl, carbamoyl, mono- or di-$C_{1-15}$-alkylaminocarbonyl, amino-$C_{1-4}$-alkylaminocarbonyl, $C_{2-4}$ alkenylaminocarbonyl, hydroxy-$C_{1-4}$-alkylaminocarbonyl, di-$C_{1-4}$-alkylaminomethyleneaminocarbonyl, $C_{3-6}$-cycloalkylamino-carbonyl, piperazinocarbonyl, morpholinocarbonyl, pyrrolidinocarbonyl, N-methylpiperazinocarbonyl, $C_{6-10}$-arylaminocarbonyl which may be substituted with $C_{1-4}$-alkyl or halogen, $C_{1-4}$-alkylaminocarbonylaminocarbonyl, hydroxy-$C_{1-4}$-alkoxy-$C_{1-4}$-alkylaminocarbonyl, $C_{1-4}$-alkylcarbonyl, $C_{1-4}$-alkylcarbonyl, $C_{6-10}$-arylarbonyl, di-$C_{1-4}$-alkoxyphosphoryland di-$C_{6-10}$-aryloxyphosphoryl group and the other group which $R_2$ and $R_3$ represent is a hydrogen atom, a hydrocarbon group of the class consisting of a $C_{1-15}$-alkyl, $C_{3-6}$-cycloalkyl, $C_{2-4}$-alkenyl, $C_{3-6}$-cycloalkenyl, $C_{6-10}$-aryl and phenyl-$C_{1-3}$-alkyl group, or a heterocyclic group of the class consisting of thienyl, triazolyl, and pyridyl, said hydrocarbon or heterocyclic groups being optionally substituted bynitro, amino, hydroxy, cyano, carbamoyl, carboxyl, sulfo, halo, trifluoromethyl, methylenedioxy, $C_{1-4}$-alkoxy, hydroxy-$C_{1-4}$-alkoxy, phenoxy, benzoyl, halobenzoylaminocarbonylamino or halophenylaminocarboxylamino group;
$X^1$ is —S— or —SO—;
$X^2$ is —S—, or a salt thereof.

11. A pesticidal composition which contains an insecticidally, acaricidally or nematocidally effective amount of 2-cyano-2-(N,N-diethylaminocarbonyl)-5-(N,N-dimethylamino)-1-3-dithiane or a salt thereof and a carrier.

12. A pesticidal composition which contains an insecticidally, acaridically or nematocidally effective amount of 2,2-dibenzoyl-5-(N,N-dimethylamino)-1,3-dithiane or a salt thereof and a carrier.

* * * * *